(12) United States Patent
Harshbarger et al.

(10) Patent No.: US 9,261,037 B2
(45) Date of Patent: Feb. 16, 2016

(54) PARTICULATE MATTER SENSOR AND SYSTEMS

(75) Inventors: Daniel R. Harshbarger, Columbus, IN (US); Ross C. Berryhill, Nashville, IN (US); James Peyton-Jones, Swarthmore, PA (US); Dieter Bender, Villanova, PA (US)

(73) Assignee: CUMMINS EMISSION SOLUTIONS, INC., Columbus, IN (US)

( * ) Notice: Subject to any disclaimer, the term of this patent is extended or adjusted under 35 U.S.C. 154(b) by 689 days.

(21) Appl. No.: 13/618,664

(22) Filed: Sep. 14, 2012
(Under 37 CFR 1.47)

(65) Prior Publication Data

US 2013/0233051 A1      Sep. 12, 2013

Related U.S. Application Data

(60) Provisional application No. 61/535,513, filed on Sep. 16, 2011.

(51) Int. Cl.
| | |
|---|---|
| *G01N 15/06* | (2006.01) |
| *F01N 11/00* | (2006.01) |
| *F02D 41/14* | (2006.01) |
| *G01M 15/10* | (2006.01) |
| *F02D 41/22* | (2006.01) |

(52) U.S. Cl.
CPC ............ *F02D 41/1466* (2013.01); *F01N 11/00* (2013.01); *G01M 15/102* (2013.01); *F01N 2550/04* (2013.01); *F01N 2560/05* (2013.01); *F01N 2900/0416* (2013.01); *F02D 41/222* (2013.01); *G01N 15/0656* (2013.01); *Y02T 10/47* (2013.01)

(58) Field of Classification Search
CPC ............ F01N 2550/04; F01N 2560/05; F01N 2900/0416; F01N 9/002; F02D 41/1466; F02D 41/222; G01N 15/0656; Y02T 10/47
See application file for complete search history.

(56) References Cited

U.S. PATENT DOCUMENTS

| | | | |
|---|---|---|---|
| 5,644,241 | A | 7/1997 | Hewelt |
| 6,392,562 | B1 | 5/2002 | Boston et al. |
| 6,928,854 | B2 | 8/2005 | Hartz et al. |
| 7,587,925 | B2 | 9/2009 | Wirth et al. |
| 2007/0056352 | A1 | 3/2007 | Birkhofer et al. |
| 2007/0125075 | A1 * | 6/2007 | Zanini-Fisher et al. ........ 60/297 |

(Continued)

FOREIGN PATENT DOCUMENTS

| | | |
|---|---|---|
| DE | 10 2005 016 132 | 10/2006 |
| WO | WO-2011/106850 | 9/2011 |

OTHER PUBLICATIONS

Extended European Search Report issued in European Patent Application No. 12184730.5, dated Feb. 13, 2013.

*Primary Examiner* — Lisa Caputo
*Assistant Examiner* — Punam Roy
(74) *Attorney, Agent, or Firm* — Foley & Lardner LLP

(57) ABSTRACT

A system including a channel; a particulate matter sensor disposed in fluid communication with the channel, the particulate matter sensor having a sensitivity that increases in response to exposure to particulate matter; and a controller coupled to the particulate matter sensor and configured to monitor the channel in response to the sensitivity of the particular matter sensor.

11 Claims, 3 Drawing Sheets

(56) References Cited

U.S. PATENT DOCUMENTS

| | | | |
|---|---|---|---|
| 2008/0000218 A1* | 1/2008 | Handler et al. | 60/273 |
| 2013/0030678 A1* | 1/2013 | Aoki | F01N 9/002 701/113 |
| 2013/0298537 A1* | 11/2013 | Aoki | F01N 3/023 60/311 |
| 2014/0305106 A1* | 10/2014 | Hashida | F01N 3/023 60/301 |

\* cited by examiner

PARTICULATE MATTER SENSOR AND SYSTEMS

CROSS REFERENCE TO RELATED APPLICATIONS

The present application claims benefit of U.S. Provisional Patent Application No. 61/535,513 filed Sep. 16, 2011, entitled PARTICULATE MATTER SENSOR AND SYSTEMS, which is incorporated herein by reference in the entirety for all purposes.

BACKGROUND

Embodiments relate to particulate matter sensors and, in particular, systems using particulate matter sensors.

Exhaust from internal combustion engines can include particulate matter. For example, diesel engines can emit soot. A diesel particulate filter can be used to reduce an amount of soot emitted.

BRIEF DESCRIPTION OF THE DRAWINGS

The description herein makes reference to the accompanying drawings wherein like reference numerals refer to like parts throughout the several views, and wherein.

DETAILED DESCRIPTION

Embodiments will be described with reference to the drawings. Although particular embodiments will be described, the scope of the following claims is not limited to these embodiments. In contrast, alterations, modifications, combinations, or the like can be made.

Figure 1:
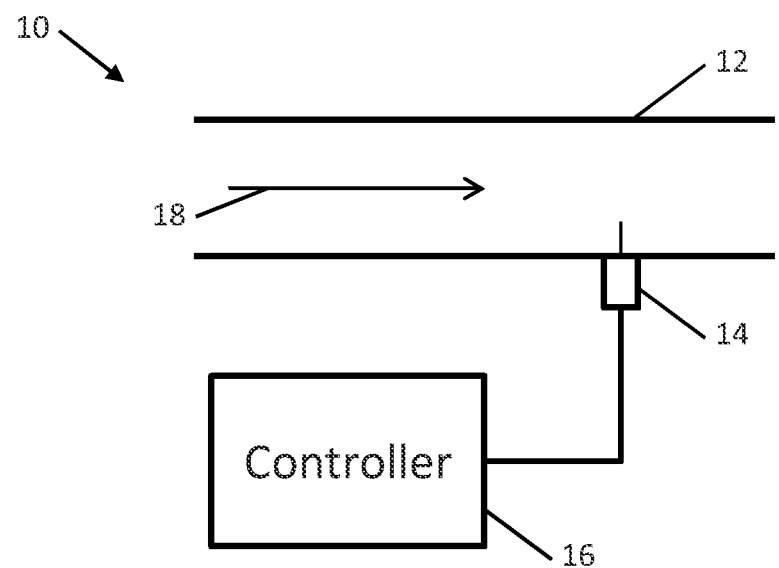
FIG. 1 is a diagram illustrating a particulate matter sensor in a particulate matter stream according to an embodiment.

FIG. 1 is a diagram illustrating a particulate matter sensor in a particulate matter stream according to an embodiment. In this embodiment, the system 10 includes a channel 12 through which a stream 18 of particulate matter can flow. For example, the channel 12 can be part of an exhaust system of an engine, vehicle, generator, or any other combustion-based device. The channel 12 can be an exhaust manifold, an exhaust pipe, an aftertreatment system, a muffler, or the like.

A particulate matter sensor 14 can be disposed in the channel 12. As illustrated, the particulate matter sensor 14 can penetrate the channel 12. However, the particulate matter sensor 14 can be disposed in other locations, such as inside the channel 12, in a side path or branch of the channel 12, or the like. In an embodiment, the particulate matter sensor 14 can be a resistivity and/or conductivity based sensor. For example, the sensor 14 can include two electrodes. The resistance between the electrodes can change based on an accumulation of particulate matter. The resistance can be measured with a variety of techniques. For example, a bias voltage and/or current can be applied to the sensor 14, a resistor network including the sensor 14, or the like. A voltage on a node of the resistor network can be measured to sense the resistance or conductance of the sensor 14. Although a resistivity based sensor has been described, any sensor architecture and the associated measurement techniques can be used, such as a capacitance based sensor, optical based sensor, or the like.

A controller 16 can be coupled to the particulate matter sensor 14 and configured to monitor the channel 12 in response to the sensitivity of the particulate matter sensor 14. The controller 16 can be any variety of devices. For example, the controller 16 can be a dedicated controller configured to solely interact with the particulate matter sensor 14. In another example, the controller 16 can be an emission control computer of a vehicle. In another example, the controller 16 can be a controller for the entire vehicle including other non-emission related subsystems.

The processing, monitoring, or the like of sensed signals can be distributed between the particulate matter sensor 14 and controller 16 as desired. For example, the sensor 14 can be configured to output a raw sensor signal that is interpreted by the controller 16. In another example, the sensor 14 can be configured to output a processed signal representative of the raw signal. In another example, the sensor 14 can be configured to output a sensitivity of the sensor 14. Furthermore, the particulate matter sensor 14 can be configured to output multiple such signals. Accordingly, although various operations, functionality, or the like are described herein as being performed by the controller 16, such operations, functionality, or the like can be distributed between the sensor 14 the controller 16 as desired.

Although a variety of outputs have been described, the particulate matter sensor 14 can include a variety of inputs. For example, the particulate matter sensor 14 can include an input associated with a heater for regeneration of the sensor 14.

Figure 2:
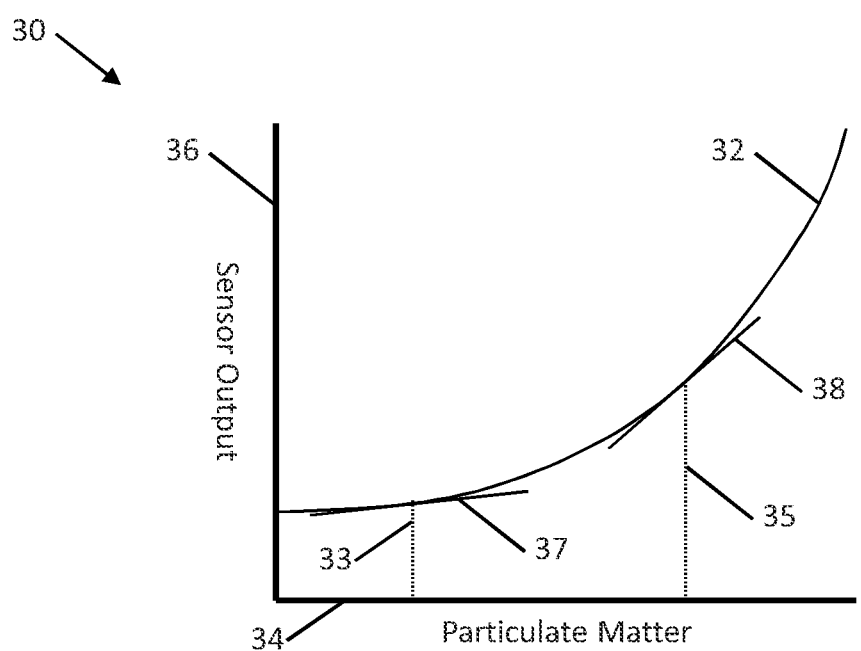
FIG. 2 is a graph showing a particulate matter sensor output versus an amount of particulate matter according to an embodiment.

FIG. 2 is a graph showing a particulate matter sensor output versus an amount of particulate matter according to an embodiment. In an embodiment, the particulate matter sensor 14 can have a sensitivity that increases in response to exposure to particulate matter. Graph 30 illustrates such a response. Axis 34 represents a magnitude of particulate matter. For example, the magnitude can be an amount of particulate matter that has passed the sensor. In another example, the magnitude can be an amount of particulate matter that has been deposited on the sensor 14.

Axis 36 represents an output of the sensor 14. As described above, the output can be a raw sensor signal, a processed sensor signal, or the like. Curve 32 represents the change in the sensor output versus the magnitude of particulate matter. In particular, as the amount of material increases, the sensitivity of the sensor increases. For example, at particulate matter magnitude 33, the sensitivity is represented by tangent 37. At particulate matter magnitude 35, the sensitivity is represented by tangent 38. The slope of tangent 38 is greater than the slope of tangent 37. Thus, for a given infinitesimal increase in particulate matter, the sensor output increases more around particulate matter magnitude 35 than at particulate matter magnitude 33. In other words, the sensitivity, or magnitude of output for a given input, increases with increasing particulate matter.

In an embodiment, a particulate matter sensor 14 can be used having a sensor with a particular affinity for a desired particulate matter, such as soot. For example, substrates, electrodes, coatings, or the like can be selected for the particular affinity. The affinity of the sensor for the particulate matter can be selected such that the affinity of the sensor to the desired particulate matter is less than an affinity of the particulate matter for itself. Accordingly, as more particulate matter is deposited on the sensor 14, the overall affinity of the sensor 14 increases.

Although a smooth curve 32 has been illustrated, an actual output of a sensor 14 in operating conditions may not increase monotonically versus particulate matter. For example, in operating conditions, the output of a sensor 14 versus increasing particulate matter may remain constant, decrease, oscillate, or the like. However, such a sensor 14 can substantially have an increasing sensitivity. That is, such transient changes can still have a net result of an increasing sensitivity. A sensor 14 having a sensitivity that increases in the net with increasing particulate matter is contemplated herein as a sensor 14 having an increasing affinity with particulate matter. The range over which the sensor 14 is determined to have an increasing affinity can be any selected range, including but not limited to increasing sensitivity over: a range of interest, an expected operating range, a manufacturer specification range of the sensor 14, and/or a range specified by a required operating range for the sensor 14 (e.g. required range to meet emissions, reliability targets, etc.)

In an embodiment, the controller 16 can be configured to determine an amount of particulate matter that has passed the particulate matter sensor in response to the sensitivity. As illustrated by curve 32 and, in particular, tangents 37 and 38, the sensitivity of the sensor 14 increases with increasing magnitudes of particulate matter. Thus, the sensitivity can be used as a proxy for the magnitude of particulate matter.

For example, the controller 16 can be configured to measure the sensor 14 output over a range of samples to measure an existing sensitivity. The controller 16 can be configured to use other factors such as fuel consumption, operating conditions, exhaust flow rates, or the like to measure the sensitivity.

Once measured, the sensitivity can be used to determine an amount of particulate matter that has passed the particulate matter sensor 14. For example, a calibration, such as a look-up table, can be used to convert the sensitivity into a magnitude of particulate matter. In another example, an equation can be used to convert the sensitivity into a magnitude of particulate matter.

As described above, an amount of particulate matter that has passed a sensor 14, been deposited on a sensor 14, or the like can change the sensitivity of the sensor 14. Accordingly, an amount of particulate matter can be passed over the sensor, deposited on the sensor 14, or the like to attain a particular sensitivity. Such an initial sensitivity, whether induced or initially present, can be used along with an existing sensitivity in the various uses of the sensitivity described herein.

Figure 3:
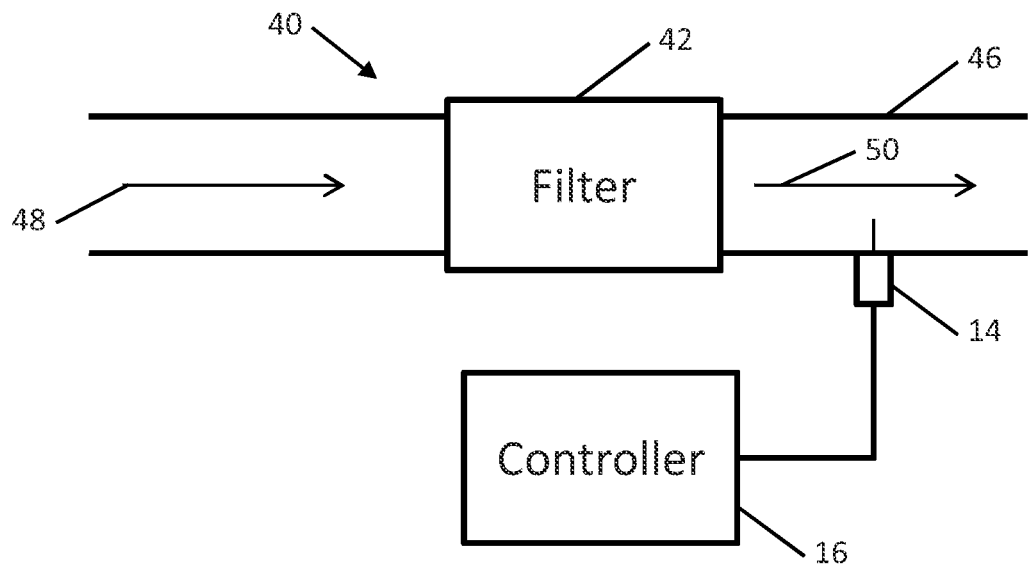
FIG. 3 is a diagram illustrating a particulate matter sensor in a filtered particulate matter stream according to an embodiment.

FIG. 3 is a diagram illustrating a particulate matter sensor in a filtered particulate matter stream according to an embodiment. In this embodiment, the system 40 includes a filter 42 disposed in the channel 46. In an example, the filter 42 can be a diesel particulate filter, an air filter, a fuel filter, or any other particulate matter filter. The filter 42 is configured to filter an incoming particulate matter stream 48 into a filtered stream 50. In this embodiment, the particulate matter sensor 14 is disposed in a downstream side of the filter 42; however, in other embodiments, the sensor 14 can be disposed on an upstream side of the filter 42, disposed on both sides, disposed in multiple locations or branches, or the like.

The controller 16 can be configured to determine if the filter 42 has failed. In particular, the controller 16 can be configured to determine if the filter has failed in response to the sensitivity of the particulate matter sensor 14. For example, as described above, the sensitivity of the particulate matter sensor 14 can be obtained. This sensitivity can be monitored over time to determine if the filter 42 has failed. For example, if a sensitivity of the particulate matter sensor 14 is substantially constant, increasing at a rate below a threshold, or the like, a determination can be made that the filter has not failed. In contrast, if the sensitivity is increasing, increasing at a rate above a threshold, or the like, a determination can be made that the filter has failed. The sensitivity values that are determined to be substantially constant will depend upon the specific application, and non-limiting examples include: sensitivity values occurring in a channel (e.g. a 1% range, 3% range, 5% range, or 10% range); sensitivity values changing less than a threshold amount in a threshold period of time; sensitivity values that change less than a specified percentage value over a threshold period of time; and/or sensitivity values that do not change more than an absolute amount high or low from a baseline sensitivity value over a selected period of time.

Although particular examples, of what would or would not indicate a failed filter 42 have been described, other factors can be considered and other thresholds can be established. For example, operating conditions, sensor status, or the like can be used. In another example, the sensitivity can be monitored over a period of time before a determination is made.

Figure 4:
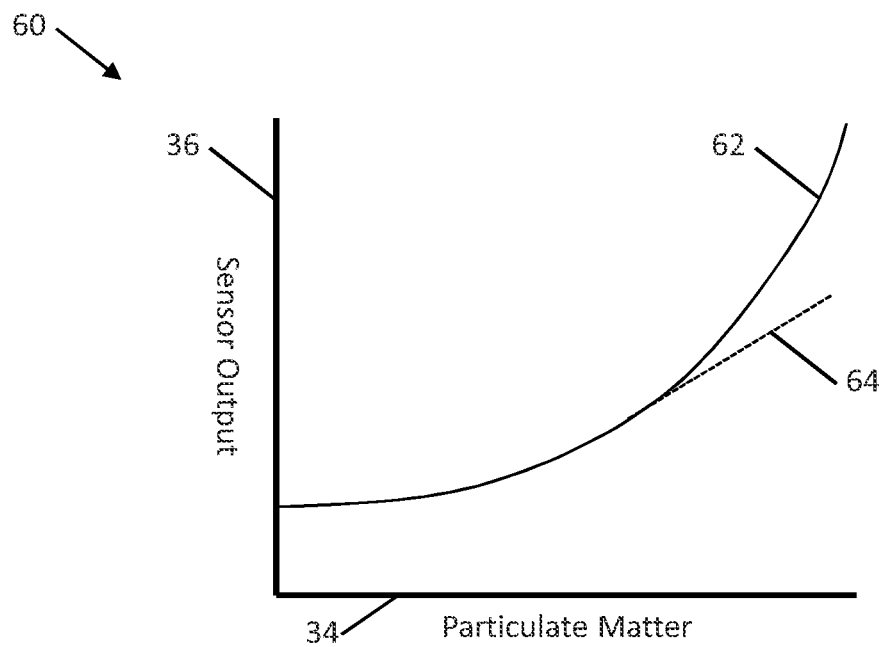
FIG. 4 is a graph showing particulate matter sensor outputs versus an amount of particulate matter according to an embodiment.

FIG. 4 is a graph showing particulate matter sensor outputs versus an amount of particulate matter according to an embodiment. Axes 34, 36 of graph 60 again represent a magnitude of particulate matter and a sensor output, respectively. Curve 62 represents a sensor 14 where the sensitivity is increasing for increasing particulate matter. However, after curve 64 represents another sensor 14 where the sensitivity has stopped increasing. In this example, the response of curve 64 has become substantially linear versus particulate matter, resulting in a substantially constant sensitivity. In other examples, the response may decrease, indicating a decreasing sensitivity. In particular, in a diesel engine system, some particulate matter, such as soot, can be burned off during a regeneration cycle of a diesel particulate filter. Particulate matter deposited on the sensor 14 may also be burned off during such an operation. However, contaminants may remain on the sensor 14 and affect the sensitivity.

In an embodiment, such a change to where a sensitivity of a sensor 14 is substantially steady or decreasing can indicate that the sensor has failed. Sensitivity values that are substantially steady or decreasing include, without limitation: sensitivity values that do not rise a threshold amount within a specified period of time; sensitivity values that do not rise a threshold percentage within a specified period of time; and/or sensitivity values that do not rise at a rate above a threshold rate within a threshold period of time. The threshold rates, amounts, and percentages are readily determined according to simple testing and data sampling for a particular sensor utilizing particulate matter that reasonably approximates the particulate matter expected in a final operating application, and are readily determined by one of skill in the art having the benefit of the disclosures herein and parameters generally known in the art. Parameters generally known in the art include, without limitation, source voltages for the sensor, service life of the sensor, exhaust gas temperature and compositions ranges expected, and electrical information for the sensor. In certain embodiments, an increasing sensitivity can indicate that the sensor 14 has not failed. Although an increasing sensitivity has been described as not a failure, some increasing sensitivity can be considered a failure. For example, a sensitivity that is increasing below a threshold rate can be considered a failure.

In another embodiment, such a change in the sensitivity can mean that the sensor 14 should be cleaned, regenerated, or the like. The sensor 14 may return to a state with increasing sensitivity after such operations. Such operations and other related information can be included in a determination if the sensor 14 has failed. For example, a number of regeneration cycles, a length of time from regeneration to an onset of substantially steady or decreasing sensitivity, or the like can be used to determine if the sensor 14 has failed.

A sensitivity of a sensor output versus a magnitude of particulate matter has been used as an example. However, the sensitivity can take other forms. For example, the magnitude of particulate matter can translate into a time of operation. That is, in an environment where the flow rate of the particulate matter in a channel 12 is substantially constant, a sensitivity versus time can be used. In another example, if a time and a time varying particulate matter density are available, such factors can be incorporated into the sensitivity of the particulate matter sensor 14.

As described above, a particulate matter sensor 14 may be regenerated from time to time. Such regeneration can be unrelated to a failure of the sensor 14. For example, a particulate matter sensor 14 can be regenerated along with a diesel particulate filter. In such circumstances, the sensitivity of the sensor 14 can change. The functionality described above can be modified to accommodate such a change in sensitivity. For example, the step change in sensitivity due to regeneration can be offset when using measurements spanning the regeneration cycle.

Figure 5:
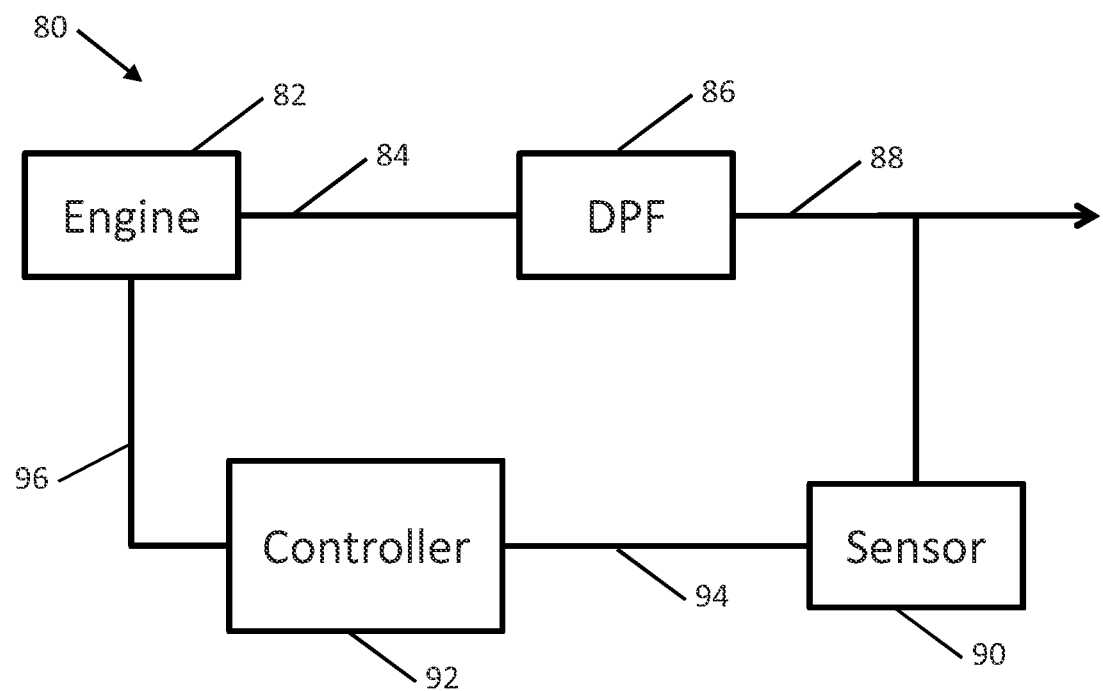
FIG. 5 is a block diagram of a vehicle with a particulate matter sensor according to an embodiment.

FIG. 5 is a block diagram of a vehicle with a particulate matter sensor according to an embodiment. In an embodiment, the vehicle 80 includes an engine 82. For example, the engine 82 can be a diesel engine. The engine 82 is configured to emit exhaust 84 to a diesel particulate filter 86. The filtered exhaust 88 can be released. Although only an engine 82 and diesel particulate filter 86 have been described, other exhaust components can be present, such as emission control devices, aftertreatment systems, turbochargers, mufflers, or the like.

A particulate matter sensor 90 is disposed such that it can sense the filtered exhaust 88. However, as described above, the particulate matter sensor 90 can be disposed in a variety of locations.

The particulate matter sensor 90 is coupled to a controller 92. The controller 92 can be configured to perform the variety of functions described above. For example, the controller 92 can monitor the diesel particulate filter 86 by monitoring a sensitivity 94 received from the particulate matter sensor 90, the controller 92 can determine if the sensor 90 has failed, or the like.

The controller 92 can be coupled to the engine 82. For example, the controller 92 can be part of an engine management system. Control signals 96 to and from the engine and/or other components can be processed by the controller 92.

Although particulate matter alone has been described in a channel, other substances can be present. For example, air, exhaust gasses, or other media supporting the particulate matter can be present.

While embodiments have been described with reference to the drawings, the sprit and scope of the following claims is not limited to the disclosed embodiments, but on the contrary, is intended to cover various modifications, combinations, and equivalent arrangements. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

The invention claimed is:

1. A system, comprising:
   a channel;
   a particulate matter sensor disposed in fluid communication with the channel, the particulate matter sensor having a sensitivity that increases in response to exposure to particulate matter; and
   a controller coupled to the particulate matter sensor and configured to:
   monitor the channel in response to the sensitivity of the particulate matter sensor, and
   determine that a filter disposed in a channel with the particulate matter sensor has not failed in response to at least one of:
   the sensitivity of the particulate matter sensor being substantially constant, and
   the sensitivity of the particulate matter sensor increasing at a rate below a threshold.

2. The system of claim 1, wherein the controller is configured to determine that the particulate matter sensor requires regeneration in response to a change in the sensitivity of the particulate matter sensor.

3. The system of claim 1, wherein the controller is configured to determine that the particulate matter sensor requires regeneration in response to a change in the sensitivity of the particulate matter sensor.

4. The system of claim 1, wherein the controller is configured to determine if a filter disposed in a channel with the particulate matter sensor has failed in response to the sensitivity of the particulate matter sensor.

5. The system of claim 1, wherein the controller is configured to monitor the channel in response to the sensitivity of the particulate matter sensor over a predetermined period of time, and to determine if a filter disposed in the channel with the particulate matter sensor has failed in response to the sensitivity of the particulate matter sensor.

6. The system of claim 1, wherein the sensitivity of the particulate matter sensor increases in response to exposure to the particulate matter over a predetermined time of operation.

7. A system, comprising:
   a channel;
   a particulate matter sensor disposed in fluid communication with the channel, the particulate matter sensor having a sensitivity that increases in response to exposure to particulate matter; and
   a controller coupled to the particulate matter sensor and configured to:
   monitor the channel in response to the sensitivity of the particulate matter sensor, and
   determine that a filter disposed in a channel with the particulate matter sensor has failed in response to at least one of:
   the sensitivity of the particulate matter sensor increasing; and
   the sensitivity of the particulate matter sensor increasing at a rate above a threshold.

8. A system, comprising:
   a channel;
   a particulate matter sensor disposed in fluid communication with the channel, the particulate matter sensor having a sensitivity that increases in response to exposure to particulate matter; and
   a controller coupled to the particulate matter sensor and configured to monitor the channel in response to the sensitivity of the particulate matter sensor;
   wherein the particulate matter sensor has an affinity for one or more types of particulate matter, and wherein the affinity to the one or more types of particulate matter is less than an affinity of the particulate matter for itself.

9. A method, comprising:
monitoring a sensitivity of a particulate matter sensor having a sensitivity that increases in response to exposure to particulate matter;
determining an amount of particulate matter deposited on the particulate matter sensor in response to the sensitivity; and
depositing particulate matter on the particulate matter sensor to attain a predetermined sensitivity.

10. The method of claim 9, further comprising:
determining if a filter disposed in a channel with the particulate matter sensor has failed in response to the sensitivity of the particulate matter sensor.

11. A method, comprising:
monitoring a sensitivity of a particulate matter sensor having a sensitivity that increases in response to exposure to particulate matter;
determining an amount of particulate matter deposited on the particulate matter sensor in response to the sensitivity; and
passing particulate matter past the particulate matter sensor to a predetermined sensitivity.

* * * * *